United States Patent [19]

Gebert et al.

[11] 4,213,986
[45] Jul. 22, 1980

[54] NOVEL DERIVATIVES OF IMIDAZOLE AND PHARMACEUTICAL COMPOSITIONS CONTAINING THEM AND METHOD OF USE

[75] Inventors: Ulrich Gebert, Kelkheim; Josef Musil, Kirchzarten-Burg; Rolf-Ortwin Weber, Wiesbaden-Naurod, all of Fed. Rep. of Germany

[73] Assignee: Hoechst Aktiengesellschaft, Frankfurt am Main, Fed. Rep. of Germany

[21] Appl. No.: 949,018

[22] Filed: Oct. 6, 1978

Related U.S. Application Data

[62] Division of Ser. No. 741,418, Nov. 12, 1976, Pat. No. 4,152,440.

[30] Foreign Application Priority Data

Nov. 2, 1976 [DE] Fed. Rep. of Germany ....... 2650231

[51] Int. Cl.$^2$ .................. A61K 31/44; A61K 31/495; A61K 31/505
[52] U.S. Cl. ..................................... 424/250; 424/251; 424/263; 542/432; 544/238; 544/323; 544/326; 544/336; 546/273
[58] Field of Search ....................... 424/263, 250, 251; 260/308 D; 544/238, 323, 326, 336; 546/276; 542/432

[56] References Cited

U.S. PATENT DOCUMENTS

| 2,470,085 | 5/1949 | Harrill et al. ................... 260/308 D |
| 2,770,620 | 11/1956 | Spieglitz et al. ................. 260/308 D |
| 3,935,209 | 1/1976 | Beard et al. ..................... 260/308 D |
| 3,941,804 | 3/1976 | Ilvespää et al. .................. 260/308 D |
| 3,992,397 | 11/1976 | Winkelmann et al. .......... 260/308 D |

*Primary Examiner*—Stanley J. Friedman
*Attorney, Agent, or Firm*—Berman, Aisenberg & Platt

[57] ABSTRACT

A physiologically-acceptable compound of one of the formulae

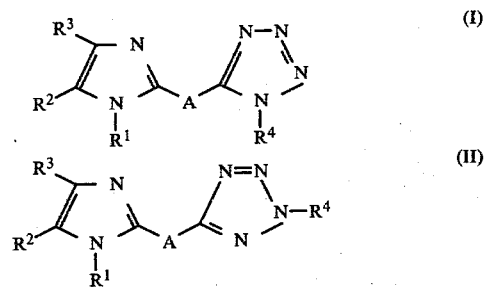

wherein
$R^1$ is a member selected from the group consisting of (a) a 6-membered heteroaromatic ring with up to two ring hetero atoms selected from the group consisting of O, N and S, at most one of which is different from nitrogen, and (b) an alkyl group containing from 1 to 4 carbon atoms and substituted by such a heteroaromatic ring;

each of $R^2$ and $R^3$ is, independently, a hydrogen atom, alkyl having up to 4 carbon atoms, substituted or unsubstituted aryl or, together with the other of $R^2$ and $R^3$, unsubstituted —CH=CH—CH=CH— or —CH=CH—CH=CH— substituted by a member selected from the group consisting of alkyl having up to 4 carbon atoms, alkoxy having up to 4 carbon atoms, haloalkyl having up to 4 carbon atoms, halo and nitro;

$R^4$ is a member selected from the group consisting of a hydrogen atom, alkyl having up to 4 carbon atoms, aryl and aralkyl having up to 4 carbon atoms in the alkyl moiety; and A is a single bond or alkylene having from 1 to 6 carbon atoms;

any substituent of substituted aryl being a member selected from the group consisting of alkyl having up to 4 carbon atoms, alkoxy having up to 4 carbon atoms, haloalkyl having up to 4 carbon atoms, halo or nitro;

or a physiologically-acceptable salt thereof and a composition containing said compounds.

8 Claims, 1 Drawing Figure

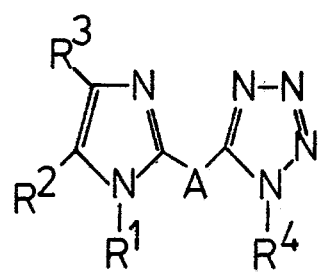 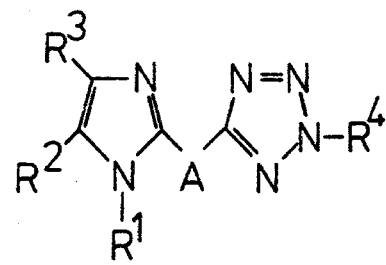
I II
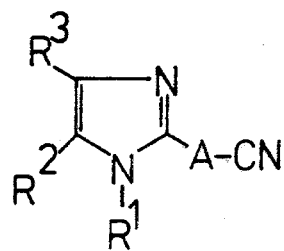 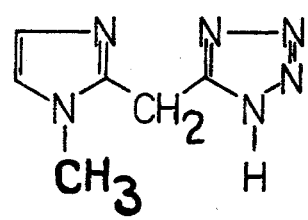
III IV
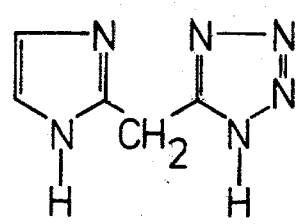 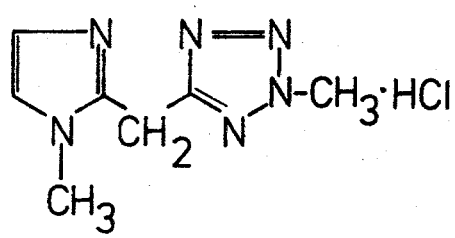
V VI
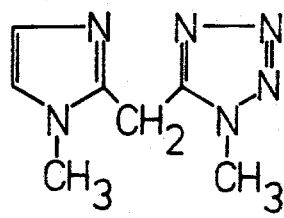 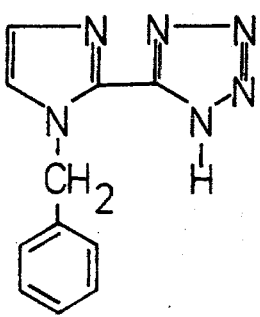
VII VIII

NOVEL DERIVATIVES OF IMIDAZOLE AND PHARMACEUTICAL COMPOSITIONS CONTAINING THEM AND METHOD OF USE

This application is a division of pending application Ser. No. 741,418, filed Nov. 12, 1976, now U.S. Pat. No. 4,152,440.

This invention relates to novel imidazole derivatives and salts thereof, processes for their preparation and pharmaceutical compositions containing these new compounds as active ingredients.

Substituted imidazoles showing pharmacological activity have been described in the literature. Thus, 2-and 5-amino-imidazole, 2-mercapto imidazoles, 2-substituted-4,5-diaryl-imidazoles, imidazolyl-(1)-alkanecarboxylic acids and the esters thereof, and cyclic 1-thiocarbamoyl-imidazoles have been described as active ingredients for the preparation of pharmaceutical compositions. The chief feature of these compounds is their anti-inflammatory activity which is sometimes accompanied by more or less powerful analgesic and/or antipyretic effects.

Furthermore, at least two 5-(2-benzimidazolyl)-tetrazoles are known which have a hydrogen atom or a methyl group at the imido nitrogen of the benzimidazole system. These compounds have been tested for a tuberculostatic activity and were found to be inactive.

The preparation of photographic emulsions by precipitating silver halide in an aqueous medium in the presence of a Z—A—X compound wherein two optionally substituted heterocyclic rings are connected to each other directly or via an alkylene group has also been described. Z and X in these compounds may represent imidazole, benzimidazole and tetrazole groups. However, an imidazolyl or benzimidazolyl-tetrazole has not been disclosed.

We have now found that by linking the imidazole system to the tetrazole ring, novel compounds are produced. The resulting compounds have interesting pharmacological properties, particularly a marked anti-uricopathic activity. They have also exhibited an analgesic effect. Moreover, very low toxicity and good gastric compatibility and the lack of central, vegetative and cardiovascular side effects have been noted.

Thus according to one aspect of the present invention there are provided compounds of the general formula

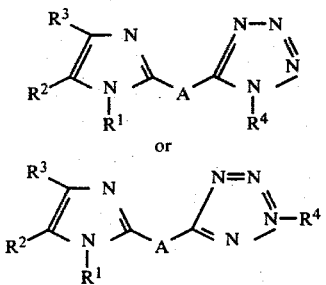

[wherein $R^1$ represents a hydrogen atom; a straight-chained or branched alkyl group containing up to 6 carbon atoms, optionally substituted by an alkoxy or phenylalkoxy group containing up to 4 carbon atoms in the alkoxy moiety; an aryl, preferably phenyl, or aralkyl group containing from 1 to 4 carbon atoms in the alkyl moiety, optionally nuclearly substituted by at least one (a) alkyl, alkoxy, or haloalkyl group each containing up to 4 carbon atoms, (b) halogen atom or (c) nitro group; a 5- or 6-membered heteroaromatic ring containing up to two hetero atoms chosen from O, N and S, at most one of which is different from nitrogen; or an alkyl group containing from 1 to 4 carbon atoms substituted by a 5- or 6-membered heteroaromatic ring containing up to 2 hetero atoms chosen from O, N and S, at most one of which is different from nitrogen;

$R^2$ and $R^3$, which may be the same or different, each represents a hydrogen atom, a straight-chained or branched alkyl group containing up to 4 carbon atoms or an aryl group, preferably phenyl, optionally substituted by at least one alkyl, alkoxy or haloalkyl group each containing up to 4 carbon atoms or halogen atom or nitro group or, taken together, $R^2$ and $R^3$ represent a —CH=CH—CH=CH— group optionally substituted by an alkyl, alkoxy or haloalkyl group containing up to 4 carbon atoms, by a halogen atom or by a nitro group;

$R^4$ represents a hydrogen atom or an alkyl, aryl or aralkyl group containing up to 4 carbon atoms in each alkyl moiety thereof; and A represents a single bond or a straight-chained or branched alkylene group containing from 1 to 6 carbon atoms; with the proviso that when A represents a single bond and $R^2$ and $R^3$ taken together represent an unsubstituted —CH=CH—CH=CH— group, then $R^1$ is other than a hydrogen atom or methyl group] and physiologically compatible salts thereof.

The salts of the compounds according to the invention may be the acid addition salts or, when $R^4$ represents hydrogen, the alkali metal, alkaline earth metal or ammonium salts, as well as those with organic bases.

The term "phenylalkoxy" (as used herein) is intended to include groups of the benzyloxy and phenethoxy type.

Suitable aralkyl groups in the compounds according to the invention include, for example, optionally substituted benzyl, phenethyl and benzhydryl; and suitable heteroaromatic groups of $R^1$ include, for example, thenyl, thienyl, furyl, furfuryl, pyridyl, picolyl, imidazolyl, imidazolylmethyl, pyrrolyl, pyrrolylmethyl, thiazolyl, thiazolylmethyl, oxazolyl, oxazolylmethyl, diazinyl, diazinylmethyl, such as pyridazinyl, pyridazinylmethyl, pyrimidinyl, pyrimidinylmethyl, pyrazinyl or pyrazinylmethyl.

Preferred compounds of formula I and II are those wherein $R^1$ represents an alkyl group with up to 3 carbon atoms, an alkoxyalkyl group or a phenylalkoxyalkyl group having at least 8 carbon atoms or an aralkyl group, optionally substituted with halogen or alkoxy, with 1 or 2 carbon atoms in each alkyl moiety and 6 carbon atoms in the aromatic moiety, or a phenyl group, optionally substituted with alkyl or haloalkyl, with 1 to 2 carbon atoms in the alkyl moiety; $R^2$ and each of $R^3$, which may be the same or different, represents an alkyl group with up to 2 carbon atoms or a phenyl group, or taken together represent a —CH=CH—CH=CH— group, optionally substituted by at least one methyl or methoxy group or a chlorine atom or a nitro group; A represents a single bond or an alkylene group with 1 to 3 carbon atoms; and $R^4$ represents a hydrogen atom or a methyl group.

Particularly preferred compounds include 2-(5-tetrazolylmethyl)-imidazole, which is optionally substituted in the 1-position of the imidazole ring with methyl, isopropyl, benzyl or o-tolyl and 1-benzyl-2-(5- tetrazolyl)-imidazole, and physiologically acceptable salts thereof.

According to a further aspect of the present invention there is provided a process for the preparation of compounds of general formula I or II (as hereinbefore defined) which comprises converting the cyano group of a compound of formula

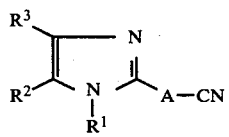 (III)

[wherein $R^1$, $R^2$, $R^3$ and A are as hereinbefore defined] into a tetrazole ring. This may be conveniently effected, for example, by converting these nitriles in conventional manner in the absence of moisture, either into imido esters or directly converting them, possibly also via the acid amides as an intermediate stage, into imide chlorides and reacting the latter with hydrogen azide or azides to form the tetrazoles of general formula I or II. The thioamides obtainable from the nitriles of formula III by the addition of hydrogen sulphide may also be cyclised by conventional processes with aluminium azide to form the corresponding tetrazoles.

In a variant of the process for preparing the compounds of general formula I or II according to the invention, which however is in several stages and is therefore less preferable, the nitriles of general formula III are converted either into the imido esters or the imide chlorides and subsequently forming the amidazones (previously termed hydrazidines) which are subsequently reacted with nitrous acid or an alkyl nitrite to bring about cyclisation. Alternatively, they may be converted into acid hydrazides which can be cyclised in an alkaline medium with diazonium salts via tetrazene intermediates. In this process compounds wherein $R^4$ is other than hydrogen are obtained.

It is also possible to react the compounds of general formula III with hydrazine to form as intermediate, amidrazone (hydrazidine) which, without being isolated, is reacted with nitrous acid or an alkyl nitrite to form the compounds according to the invention.

Nitrilium salts obtained by alkylating the nitriles III, e.g. with trialkyl oxonium salts, also react with azides to form tetrazoles of formulae I and II.

The amidines, which are easily prepared from compounds of formula III via the imido esters or imide chlorides with ammonia, may also be reacted with nitrous acid to form intermediate products which have a nitroso group at both nitrogen atoms and which are then cyclised under reductive conditions e.g. in the presence of sodium amalgam to form the compounds of general formula I or II.

The preferred process for preparing the compounds of the invention, however, is the one-step reaction of the nitriles III with azides or free hydrazoic acid to form products of formula I or II with a tetrazole ring, wherein $R^4$ represents hydrogen, whereupon these products are optionally alkylated, arylated or aralkylated with conventional alkylating, arylating or aralkylating agents to form the group $R^4$ and are then isolated. By adding physiologically compatible acids, the corresponding acid addition salts may, if desired, be prepared or, if $R^4$ represents hydrogen, the alkali metal, alkaline earth metal, or ammonium and organic base salts may alternatively be prepared in conventional fashion.

This one-step reaction of the nitriles III to form the compounds according to the invention, may also be carried out, for example, by preparing hydrazoic acid separately and then effecting the cycloaddition to the cyano compound of formula III in solution. Suitable solvents being, for example, alcohols, aromatic hydrocarbons or aprotic solvents listed below. The reaction conveniently takes place in a closed vessel at elevated temperatures, e.g. at 80° to 150° C., preferably between 100° and 150° C. Suitable alcohols include, for example, monohydric alochols containing from 1 to 6 carbon atoms, such as methanol, ethanol, the propanols, butanols, pentanols and hexanols, and suitable aromatic hydrocarbons are for example benzene, toluene and xylene. It is also possible to effect the reaction without separate hydrazoic acid preparation and thus react the nitriles of formula III, without any difficulty, by refluxing with alkali azides, for example sodium azide, in mixtures of glacial acetic acid and an alcohol. In both cases, the reaction may last up to several days. It is particularly advantageous to prepare ammonium azide and/or hydrazoic acid from sodium azide and ammonium salts of strong acids, for example, ammonium bromide, and preferably ammonium chloride, in situ, and react this with the compounds of formula III, for example, for 2 to 24 hours, and consequently obtain the tetrazoles in good yield. Preferably, aprotic solvents, particularly dimethylformamide, but also dimethyl sulphoxide, are used for this reaction, these solvents being capable of dissolving inorganic azides to a remarkable degree. This reaction is preferably carried out at temperatures of from 80° to 150° C., and advantageously from 100° to 130° C. The reaction is conveniently essentially catalysed by acids such as sulphonic acids, excess hydrazoic acid or Lewis acids, for example $BF_3$ or $AlCl_3$. The isolation of the desired end products is conveniently effected by separating the inorganic salts by filtration, after cooling, removing the solvent by evaporation under reduced pressure and recrystallising the residue from a suitable solvent, either directly or after conversion into a salt. Suitable solvents include, for example, water, alcohols, carboxylic acid esters and amides, ethers, ketones, nitriles and sulphoxides, either along or in admixture.

The nitriles of formula III used as starting materials need not always be used per se in the reaction, but may also be prepared as an intermediate in situ from various pre-products known from the literature, for example, from the corresponding imidazole aldehydes and hydrazoic acid (by the Schmidt rearrangement), or obtained from an aldoxime by dehydration, e.g. in hot dimethylformamide. Thus, it is not essential to isolate the nitrile obtained, indeed, it may be converted in situ directly into the tetrazole in solution.

For the alkylation of the tetrazole ring of the compounds of general formula I or II, conventional alkylating agents may, if desired, be used. In particular, alkyl halides and dialkyl sulphates will generally be used when starting with the alkali metal or alkaline earth metal salts of the compounds according to the invention. Other suitable alkylating agents include diazoalkanes, e.g. diazomethane, -ethane, -propane or -butane, which are preferably reacted directly with the tetrazoles in suitable organic solvents. It has proved particularly advantageous to work in an alcoholic solution. When working with diazoalkanes, the alcoholic solution to which the ethereal diazoalkane solution is added, for example, at temperatures between −10° and about +30° C., may contain a minor amount, e.g. up to 10% by volume, of water based on the total amount of solvent.

Generally, in all the variations of the process according to the invention, mixtures of 1- and 2-substituted products of formula I or II are obtained, which, if desired, can be separated by conventional methods such as, for example, fractional distillation, fractional crystallisation and/or preparative column chromatography.

Compounds of formula I and II wherein $R^1$ is hydrogen may also be prepared from those products according to the invention wherein $R^1$ represents a removable group. Examples of radicals which are easily removable include, for example, the alkoxymethyl and aralkyloxymethyl groups; preferably a methoxy methyl or benzyloxymethyl group (which may be split off hydrolytically) or, for example, a benzyl group, which may, for example, be split off with sodium in liquid ammonia or preferably with catalytically activated hydrogen i.e. hydrogenolytically.

The physiologically acceptable salts of the compounds of formula I and II may, if desired, be prepared in per se known manner. To form stable, non-toxic acid addition salts, both inorganic and organic acids may be used, such as, for example, hydrochloric, hydrobromic, sulphuric, phosphoric, methanesulphonic, benzenesulphonic and p-toluenesulphonic acids. The compounds wherein $R^4$ represents a hydrogen atom form, with basic reagents such as hydroxides, alcoholates, carbonates and hydrogen carbonates, stable, substantially water-soluble alkali metal and alkaline earth metal salts. Water-soluble salts which are virtually neutral can, if desired, be prepared with special organic bases, for example ethanolamine, diethanolamine, tris-(hydroxymethyl) aminomethane or N-methylglucamine.

The new compounds of general formula I and II and their physiologically acceptable salts can be used as pharmaceutical compositions owing to their pharmacological properties, and they may be used either alone or mixed with suitable carriers.

Thus according to a further aspect of the invention there are provided pharmaceutical compositions for human and veterinary treatment comprising, as active ingredient, at least one compound of formula I or II (as hereinbefore defined) or a physiologically acceptable salt thereof in association with a pharmaceutically acceptable carrier or excipient.

The compositions may, if desired, be administered orally, rectally or parenterally but oral administration is preferred. Suitable forms of administration include, for example, granules, powders, tablets, capsules, for example in the form of microcapsules, suppositories, syrups, emulsions, suspensions, drops or injectable solutions and sustained release forms.

Examples of excipients frequently used in compositions according to the invention include, for example, magnesium carbonate, various types of sugar and starch, cellulose derivatives, gelatin, animal and vegetable oils, polyethyleneglycol and conventional solvents.

If desired, the compositions according to the invention may be administered in dosage unit form. Tablets, capsules, suppositories and ampoules are examples of suitable dosage unit forms. Each dosage unit may conveniently contain up to 1000 mg, but preferably from 10 to 200 mg of the active ingredient according to the invention.

For treating purine metabolic disorders (see Table 1) doses of from 0.1 to 100 mg of active ingredient per kg of of body weight, preferably 1 to 50 mg/kg, are conveniently administered, depending on the activity in humans. This may be done in single doses or in subdivided doses.

For an adult weighing 70 kg, the daily dosage is thus between 7 and 7000 mg, preferably 100 to 500 mg. In certain cases, higher or lower doses may be suitable.

Compounds of formula I and II and their salts may, if desired, be formulated into pharmaceutical compositions additionally comprising one or more further active ingredients. Suitable further active ingredients include, for example, antiphlogistics, analgesics, diuretics, antihypertensives, spasmolytics, vitamins and caffein.

The compounds of formula I and II according to the invention meet all the requirements of good antiuricopathics. Thus, in addition to a strong, balanced uricosuric and hypouricaemic activity, they were at the same time seen to have a favourable effect on kidney function, such as an increase in diuresis, increased saluresis and an increase in separation of endogenous creatinin.

This good pharmacological effect on purine metabolism which is shown by an increased renal separation of uric acid, inhibition of the synthesis of uric acid de novo in the liver and an increase in the uric acid clearance value (urine value: serum value), was demonstrated in various model situations in male Wistar rats without any harmful side effects on lipid metabolism, the cardiovascular system and the intestinal tract. The compounds may therefore be useful as therapeutic agents for various disorders of purine metabolism, particularly in treating primary and secondary gout. Table 1 gives a comprehensive survey of the possible causes of hyperuricaemia.

In the developed countries, the complaints listed in Table 1 occur in approximately 2% of the male population and 0.2 to 0.7% of the female population. The frequency of this type of complaint is tending to increase. The therapy of hyperuricaemia should be regarded not only as a necessary correction of genuine metabolic disorders but rather as the elimination of one of the many risk factors of arteriosclerotic complaints.

TABLE I:

| Pathophysiological Causes of Hyperuricaemia | |
|---|---|
| A. Increased synthesis of uric acid | |
| (a) hyperproductive gout | 1 - increased activity of de-novo synthesis (e.g. phospho-ribosylpyrophosphate synthetase) 2 - overeating - increased calorie intake |
| (b) Lesh-Nyhan syndrome, genetic enzyme deficiency | lack of hypoxanthine-guanine phospho-ribosyl transferase. |
| (c) Lymphoproliferative complaints | |
| (d) Cytostatic therapy | |
| (e) Glycose storage disease | |
| (f) Sickle cell anaemia | |
| B. Reduction in renal separation of uric acid | |
| (a) all diseases of the kidney which lead to a reduction in glomerular filtration or tubular secretion, particularly in: | 1. acute kidney failure (haemodialysis) 2. lead poisoning 3. as a result of the hyperuricaemia mentioned in A: occurrence of interstitial nephritis- disorders of regulatory functions of the kidney |

TABLE I:-continued
Pathophysiological Causes of Hyperuricaemia (b) competitive inhibition of separation by other organic compounds of pharmaceuticals
1. thiazide diuretics, paraaminohippuric acid, uricosurics in low dosages
2. lactazidose
3. ketoazidose
4. glycogen storage disease C. Metabolic or circulatory complaints
1. disorders of lipid metabolism
2. diabetes
3. hypertonia
4. coronary sclerosis The uricosuric and hypouricaemic activity can be demonstrated by experiments on the Oxonat rat (G. Bonardi and A. Vidi, Sci. Pharm. Res. Comm. 5, 125 (1973); R. Bluestone et al, Israel J. Med. Sci. 9,5 (1973) and J. Musil and J. Sandow, "Amino Acids and Uric Acid Transport" (Editor S. Silbernagl et al), Georg Thieme Verlag, Stuttgart 1976, pp. 227–236). In this test series, the uricase activity of the rats' livers is inhibited by the application of potassium oxonate (potassium salt of 2,4-dihydroxy-1,3,5-triazine-(6)-carboxylic acid) and thus a gout-like disorder of the purine metabolism is induced. The animals are tested in two different ways.

1. Diuresis test 18 hours before the start of the test, the animals were placed separately in metabolism cages. At the same time they were offered unlimited quantitites of a 0.5% potassium oxonate solution to drink. On the 1st day of the test, first the urine samples collected were removed (control value) then the substances to be tested were administered in a 0.5% potassium oxonate solution by oesophageal tube into the stomach. The same operation was repeated on the 2nd day of the test. After removal of the 24 hour urine (1st sample after administration of the preparation) the test substances were administered a second time by oesophageal tube. On the 3rd day of the test, the animals were killed and bled, immediately after the urine samples from the preceding 24 hours had been collected (2nd sample after administration of the preparation). Both in the serum obtained and also in the urine samles, the concentration of uric acid was determined enzymatically, using the uricase method (Uricaquant, Boehringer Mannheim), together with a large number of metabolic parameters.

2. Combined metabolic test

This test series differs from the diuresis test described in (1) only in the method of administration of the uricase inhibitor. The animals drink water throughout the test and are given the potassium oxonate in a special feed mixture consisting of normal standard rat food to which 5% fructose, 3% uric acid, 2% potassium oxonate and 0.1% sweetener have been added. The administration of the preparations to be tested and the analysis of the urine samples from the 1st, 2nd and 3rd days of the test and of the scrum samples obtained on the 3rd day of the test were carried out as described in the diuresis test.

The results of both sets of tests are shown in Table 2. They indicate that the compounds according to the invention significantly increase the separation of uric acid in urine and reduce the concentration of uric acid in serum, and are superior to the comparison preparation Allopurinol. A comparison of the serum-uric acid values shows that the compounds listed, in doses of 25 mg/kg, by oral route, have an activity at least twice as strong as oral administration of 50 mg/kg of the comparison preparation. Another advantage of the compounds according to the invention lies in their extremely low toxicity. Thus, the acute toxicity ($LD_{50}$) in rats for oral administration by oesophageal tube determined from the mortality obtained within 7 days is, for example, more than 3150 and 4000 mg/kg for the compounds of Examples 1 and 24, respectively.

TABLE 2:

| Test | Compound of Example | n | Dosage in mg/kg | Antiuricopathic activity Separation of uric acid in the urine 1st day | 2nd day | 3rd day | Serum - uric acid mg % | % of control |
|---|---|---|---|---|---|---|---|---|
| 1 | Control Group | 8 | — | 2.89 ± 1.46 | 3.04 ± 1.53 | 3.32 ± 1.22 | 3.50 ± 1.15 | — |
|   | 24 | 8 | 25 | 2.56 ± 1.14 | 3.97 ± 1.44 | 3.47 ± 1.31 | *2.41 ± 0.98 | −31 |
| 2 | Control Group | 8 | — | 2.04 ± 1.02 | 2.58 ± 0.95 | 1.78 ± 1.40 | 8.64 ± 3.51 | — |
|   | 1 | 8 | 25 | 1.47 ± 0.60 | 3.30 ± 2.12 | 3.32 ± 1.94 | *4.83 ± 1.69 | −44 |
|   | 3 | 8 | 25 | 1.68 ± 0.51 | 2.25 ± 0.41 | 4.18 ± 2.47 | 6.97 ± 2.07 | −19 |
|   | 5 | 8 | 25 | 1.78 ± 0.92 | 2.76 ± 1.21 | 2.28 ± 1.31 | 6.05 ± 1.96 | −30 |
|   | 11 | 8 | 25 | 1.12 ± 0.64 | 2.24 ± 0.57 | 2.33 ± 1.70 | 6.00 ± 1.73 | −31 |
|   | 24 | 8 | 25 | 1.81 ± 0.61 | 2.04 ± 0.80 | 2.51 ± 1.55 | 6.07 ± 1.63 | −30 |
|   | Control Group | 8 | — | 0.81 ± 0.16 | 2.68 ± 1.73 | 3.45 ± 1.26 | 6.70 ± 0.89 | — |
|   | Allopurinol+ | 8 | 50 | 0.99 ± 0.51 | 2.16 ± 0.81 | 3.82 ± 1.59 | 6.21 ± 0.76 | −7 |

*stat. significant p<0.05 (Duncan Test)
+1 H-Pyrazolo[3,4-]pyrimidine-4-ol

The following Examples serve to illustrate the preparation of compounds of general formula I and II according to the invention. The structures of the compounds described were determined by elemental analysis, and i.r. and proton-n.m.r. spectroscopy.

1. 1-Methyl-2-(5-tetrazolylmethyl)-imidazole (formula IV (cf. formula sheet))

A mixture of 100 g (0.83 mol) of 1-methyl-2-cyanomethylimidazol 80.5 g (1.24 mol) of sodium azide and 66.2 g (1.24 mol) of ammonium chloride in 900 ml of dry dimethyl formamide is heated to 120°–130° C. for 17 hours, with stirring. It is left to cool, precipitated salts filtered off and the solvent distilled off under reduced pressure. The residue is recrystallised from methanol at boiling heat with the addition of some ether.

Yield: 114 g (84% of theory), m.p. 191°–192° C.;

Analysis: calculated for $C_6H_8N_6$: C 43.90; H 4.91; N 51.19. found: C 43.70; H 4,81; N 51.02.

The compounds listed in Table 3 were prepared as in Example 1, it proving advantageous to free the water-insoluble end products from salts by washing with water before recrystallisation.

| Example | Product | Starting Material | M.p (°C.) |
|---|---|---|---|
| 2 | 1-Ethyl-2-(5-tetrazolylmethyl)-imidazole | 1-Ethyl-2-cyanomethylimidazole | 158–159 |
| 3 | 1-Isopropyl-2-(5-tetrazolylmethyl)-imidazole | 1-Isopropyl-2-cyanomethyl-imidazole | 240–241 |
| 4 | 1-Methoxymethyl-2-(5-tetrazolylmethyl)-imidazole | 1-Methoxymethyl-2-cyano-methylimidazole | 124–125 |
| 5 | 1-benzyl-2-(5-tetrazolylmethyl)-imidazole | 1-Benzyl-2-cyanomethylimidazole | 155 |
| 6 | 1-(1-Phenylethyl)-2-(5-tetrazolylmethyl)-imidazole | 1-(1-Phenylethyl)-2-cyano-methylimidazole | 134–135 |
| 7 | 1-(2-Phenylethyl)-2-(5-tetrazolylmethyl)-imidazole | 1-(2-Phenylethyl)-2-cyano-methylimidazole | 155–156 |
| 8 | 1-(4-Chlorobenzyl)-2-(5-tetrazolylmethyl)-imidazole | 1-(4-Chlorobenzyl)-2-cyano-methylimidazole | 182–183 |
| 9 | 1-(4-Methoxybenzyl)-2-(5-tetrazolylmethyl)-imidazole | 1-(4-Methoxybenzyl)-2-cyano-methylimidazole | 176–177 |
| 10 | 1-Phenyl-2-(5-tetrazolylmethyl)-imidazole | 1-Phenyl-2-cyanomethylimidazole | 190–191 |
| 11 | 1-(o-Tolyl)-2-(5-tetrazolylmethyl)-imidazole | 1-(o-Tolyl)-2-cyanomethyl-imidazole | 180–181 |
| 12 | 1-(3-Trifluoromethyl-phenyl)-2-(5-tetrazolylmethyl)-imidazole | 1-(3-Trifluoromethyl-phenyl)-2-cyanomethylimidazole | 159–160 |
| 13 (a) | 2-(5-Tetrazolylmethyl)-imidazole | 2-Cyanomethylimidazole | 232 (decomp.) |
| 14 | 1,4,5-Trimethyl-2-(5-tetrazolylmethyl)-imidazole | 1,4,5-Trimethyl-2-cyanomethyl-imidazole | 173–174 |
| 6 (a) | 1-(1-Phenylethyl)-2-(5-tetrazolylmethyl)-imidazole, sodium salt, 1 H$_2$O | | 147–148 |
| 15 | 1-Methyl-4,5-diphenyl-2-(5-tetrazolylmethyl)-imidazole | 1-Methyl-4,5-diphenyl-2-cyano-methylimidazole | 226–228 |
| 16 | 2-(5-Tetrazolylmethyl)-benzimidazole 2-(5-Tetrazolylmethyl)-sodium salt.½ H$_2$O | 2-Cyanomethyl-benzimidazole | 273 (decomp.) 112–114 |
| 17 | 1-Methyl-2-(5-tetrazolylmethyl)-benzimidazole | 1-Methyl-2-cyanomethylbenz-imidazole | 266–268 |
| 18 | 1-Benzyl-2-(5-tetrazolylmethyl)-benzimidazole | 1-Benzyl-2-cyanomethyl-benz-imidazole | 200–202 |
| 19 | 5-Methyl-2-(5-tetrazolylmethyl)-benzimidazole | 5-Methyl-2-cyanomethyl-benz-imidazole | 246 (decomp.) |
| 20 | 5-Methoxy-2-(5-tetrazolylmethyl)-benzimidazole | 5-Methoxy-2-cyanomethyl-benz-imidazole | 256–258 (decomp.) |
| 21 | 5-Chloro-2-(5-tetrazolylmethyl)-benzimidazole | 5-Chloro-2-cyanomethyl-benzimi-dazole | 180–181 (decomp.) |
| 22 | 5-Nitro-2-(5-tetrazolylmethyl)-benzimidazole | 5-Nitro-2-cyanomethyl-benzimi-dazole | 110–112 |
| 23 | 1-Methyl-2-(5-tetrazolyl)-imidazole | 1-Methyl-2-cyanimidazole | 279–281 (decomp.) |
| 24 (a) | 1-Benzyl-2-(5-tetrazolyl)-imidazole 1-Benzyl-2-(5-tetrazolyl)-sodium salt | 1-Benzyl-2-cyanimidazole | 276–278 335–336 |
| 24 (a) | 1-Benzyl-2-(5-tetrazolyl)-imidazole-ethanol amine salt | | 114–115 |
| 25 (a) | 2-(5-Tetrazolyl)-imidazole | 2-Cyanoimidazole | 318–320 (decomp.) |
| 26 | 1-Phenyl-2-(5-tetrazolyl)-imidazole | 1-Phenyl-2-cyanoimidazole | 239–240 |
| 27 | 1-Benzyl-2-(5-tetrazolyl)-benzimidazole | 1-Benzyl-2-cyanobenzimidazole | 262–263 (decomp.) |
| 28 | 1-Methyl-2-[1-methyl-1-(5-tetrazolyl)-ethyl]-imidazole | 1-Methyl-2-(1-cyano-1-methyl-ethyl)-imidazole | 212–214 (decomp.) |
| 29 | 1-Methyl-2-[1-(5-tetrazolyl)-ethyl]-imidazole | 1-Methyl-2-(1-cyanoethyl)-imidazole | 201–202 |
| 30 | 1-Methyl-2-[2-(5-tetrazolyl)-ethyl]-imidazole | 1-Methyl-2-(2-cyanoethyl)-imidazole | 176–177 |
| 31 | 1-Benzyl-4,5-diphenyl-2-(5-tetrazolylmethyl)-imidazole | 1-Benzyl-4,5-diphenyl-2-cyano-methylimidazole | 203–205 |
| 32 | 1-Isopropyl-2-(5-tetrazolyl)-imidazole | 1-Isopropyl-2-cyanoimidazole | 274–275 |
| 33 | 1-(1-Phenylethyl)-2-(5-tetrazolyl)-imidazole | 1-(1-Phenylethyl)-2-cyanoimidazole | 235–236 |
| 34 | 1-(2-Phenylethyl)-2-(5-tetrazolyl)-imidazole | 1-(2-Phenylethyl)-2-cyanoimidazole | 273–274 |
| 35 | 1-Benzhydryl-2-(5-tetrazolyl)-imidazole | 1-Benzhydryl-2-cyanoimidazole | 222–223 |
| 36 | 1-(4-Methylbenzyl)-2-(5-tetrazolyl)-imidazole | 1-(4-Methylbenzyl)-2-cyanoimidazole | 269–270 |
| 37 | 1-(2,4,6-Trimethylbenzyl)-2-(5-tetrazolyl)-imidazole | 1-(2,4,6-Trimethylbenzyl)-2-cyano-imidazole | 281–283 |
| 38 | 1-(3-Methoxybenzyl)-2-(5-tetrazolyl)-imidazole | 1-(3-Methoxybenzyl)-2-cyanoimidazole | 273–274 (decomp.) |
| 39 | 1-(4-Methoxybenzyl)-2-(5-tetrazolyl)-imidazole | 1-(4-Methoxybenzyl)-2-cyanoimidazole | 278–280 (decomp.) |

| Example | Product | Starting product | Melting point °C |
|---|---|---|---|
| 40 | 1-(3-Trifluoromethyl-benzyl)-2-(5-tetrazolyl)-imidazole | 1-(3-Trifluoromethyl-benzyl)-2-cyanoimidazole | 279–280 |
| 41 | 1-(4-Chlorobenzyl)-2-(5-tetrazolyl)-imidazole | 1-(4-Chlorobenzyl)-2-cyanoimidazole | 296–298 (decomp.) |
| 42 | 1-(2,6-Dichlorobenzyl)-2-(5-tetrazolyl)-imidazole | 1-(2,6-Dichlorobenzyl)-2-cyano-imidazole | 288–290 (decomp.) |

| 43 | 1-Benzyl-4,5-diphenyl-2-(5-tetrazolyl)-imidazole | 1-Benzyl-4,5-diphenyl-2-cyano-imidazole | 184–185 |
| 44 | 1-Benzyl-4,5-di-(4-methoxyphenyl)-2-(5-tetrazolyl)-imidazole | 1-(Benzyl-4,5-di-(4-methoxyphenyl)-2-cyanoimidazole | 139–140 |
| 45 | 1-(2-Thenyl)-2-(5-tetrazolylmethyl)-imidazole | 1-(2-Thenyl)-2-cyanomethyl)-imidazole | 134–135 |
| 46 | 1-(2-Thenyl)-2-(5-tetrazolyl)-imidazole | 1-(2-Thenyl)-2-cyano-imidazole | 267–268 |
| 47 | 1-(2-Pyridyl)-2-(5-tetrazolyl)-imidazole | 1-(2-Pyridyl)-2-cyano-imidazole | 259–260 (decomp.) |
| 48 | 1-(2-Picolyl)-2-(5-tetrazolyl)-imidazole | 1-(2-Picolyl)-2-cyano-imidazole | 246–247 |

EXAMPLE 13(b)

2-(5-Tetrazolylmethyl)-imidazole (formula V (cf. formula sheet))

A solution of 72.1 g (0.3 mol) of 1-benzyl-2-(5-tetrazolylmethyl)-imidazole (cf. Example 5) in 600 ml of methanol is prepared and after flushing the apparatus with nitrogen a slow current of hydrogen is passed through the solution to which 15 g of palladium/active charcoal (10% Pd) have been added with constant stirring at 40°–50° C. After about 7 hours, the hydrogenolytic debenzylation is complete. The catalyst is filtered from the hot solution, washed several times with boiling methanol and the filtrate is evaporated to dryness under reduced pressure. The residue is recrystallised from methanol/ether. Yield: 36.5 g (81% of theory), m.p. 232° C. (decomposition);

Analysis: calculated for $C_5H_6N_6$: C 40.00; H 4.03; N 55.98. found: C 40.23; H 4.10; N 55.99.

EXAMPLE 13(c)

2-(5-Tetrazolylmethyl)-imidazole

Prepared by hydrolytic demethoxymethylation of 1-methoxymethyl-2-(5-tetrazolylmethyl)-imidazole of Example 4 as follows:

8.14 g (41.9 mmol) of 1-methoxymethyl-2-(5-tetrazolylmethyl)-imidazole are refluxed in a mixture of 85 ml glacial acetic acid, 8.5 ml of water and 8.5 ml of conc. hydrochloric acid for 24 hours. The mixture is then concentrated in vacuo and the residue rapidly dried to a far extent in a high vacuum over potassium hydroxide and conc. sulphuric acid. The acid addition salt obtained is decomposed with the stoichiometric quantity of sodium ethoxide in an ethanolic solution. After removal of the sodium chloride precipitated, the solvent is distilled off and the residue recrystallised from methanol at boiling heat with the addition of a little ether.

Yield: 4.4 g (70% of theory), m.p. 223°–234° C. (decomp.);

Analysis: calculated: C 40.00; H 4.03; N 55.98. found: C 40.10; H 4.06; N 56.11.

EXAMPLE 24(b)

1-Benzyl-2-(5-tetrazolyl)-imidazole (formula VIII (cf. formula sheet))

3.66 g (0.02 mol) of 1-benzyl-2-cyanoimidazole are added in portions to 20 ml of conc. sulphuric acid, the temperature being kept below 35° C. by cooling. The mixture is stirred overnight at room temperature. The reaction mixture is then poured onto ice and aq. ammonia added until alkaline. The precipitate formed is removed by suction filtration washed with water, dried and stirred thoroughly with 4.2 g (0.02 mol) of phosphorus pentachloride, in the absence of moisture. On heating to about 100° C. for one hour, a clear reddish-brown mixture is formed, from which the phosphorus oxide trichloride is removed by distillation under reduced pressure. The remaining imide chloride/hydrochloride is taken up in 50 ml of dry dimethylformamide and, after the addition of 6.4 g (0.12 mol) of ammonium chloride and 7.8 g (0.12 mol) of sodium azide, it is heated to 120°–130° C. for 5 hours, with stirring. After cooling, the reaction mixture is mixed with water, the precipitated product is filtered off and recrystallised from dimethylformamide.

Yield: 2.8 g (62% of theory): m.p. 274°–276° C.;

Analysis: calculated for $C_{11}H_{10}N_6$: C 58.40; H 4.45; N 37.15. found: C 58.29; H 4.35; N 37.16.

EXAMPLE 24(c)

1-Benzyl-2-(5-tetrazolyl)-imidazole

Obtained by reacting 9.3 g (0.05 mol) of 1-benzyl-2-formylimidazole (see Liebigs Ann. Chem. 718 (1968) pp. 249–259) with 8.0 g (0.15 mol) of ammonium chloride and 9.8 g (0.15 mol) of sodium azide in 50 ml of dimethylformamide at 120°–130° C. The isolation of the 1-benzyl-2-cyanoimidazole intermediate (obtained by Schmidt-rearrangement) may be omitted, since this compound adds excess hydrazoic acid to the tetrazole in situ. After 20 hours, it is cooled, and 500 ml of water are added, the precipitate formed filtered off and recrystallised several times from dimethylformamide. M.p. 274°–275° C.

EXAMPLE 24(d)

1-Benzyl-2-(5-tetrazolyl)-imidazole

Obtained by the addition of hydrazoic acid to 1-benzyl-2-cyanoimidazole produced as an intermediate from O-tosylated 1-benzyl-2-imidazolyl-carbaldoxime, whilst splitting off p-toluenesulphonic acid. 4.0 g (0.02 mol) of 1-benzyl-2-imidazolylcarbaldoxime (see Liebigs Ann. Chem. 718, (1968) pp. 249–259) are suspended in 20 ml of methanol, a solution of 0.46 g (0.02 gram atom) of sodium in 10 ml of methanol is added and 3.8 (0.02 mol) of p-toluensulphonic acid chloride is added to the now clear solution with stirring. It is then evaporated to dryness under reduced pressure, the residue is taken up in 20 ml of dimethylformamide, 6.5 g (0.1 mol) of sodium azide are added and the mixture is stirred at 130° C. for 18 hours. After cooling, 200 ml of water are added, the mixture neutralised with 2 N hydrochloric acid, the obtained precipitate suction filtered off and the salt washed out with water. By recrystallisation of dimethylformamide, 3.7 g (81.8% of theory) of analytically pure product are obrained. M.p. 278°–279° C.

The dehydration of the oxime (2.0 g, 0.01 mol) to form 1-benzyl-2-cyanoimidazole may also be effected without previous conversion into the O-tosyl derivative by simply heating it for several hours in dimethylformamide (20 ml) to 130° C. (cf. for this Z. Chem. 15 (1975), whilst in the presence of stoichiometric quantities of sodium azide (0.65 g, 0.01 mol) and p-toluenesulphonic acid monohydrate (1.0 g, 0.01 mol) the desired tetrazole is formed directly, m.p. 279° C.

If in the above method the p-toluenesulphonic acid is replaced with ammonium chloride, the product of formula VIII is obtained in a good yield:

4.0 g (0.02 mol) of 1-benzyl-2-imidazolylcarbaldoxime are dissolved in 20 ml of dimethylformamide and, after the addition of 2.0 g (0.03 mol) of sodium azide and 1.6 g (0.03 mol) of ammonium chloride, the mixture is refluxed for 8 hours. It is then left to cool, 100 ml of water are added, it is acidified with acetic acid, the precipitated solid is removed and recrystallised from dimethylformamide.

Yield: 4.2 g (92.8% of theory); m.p. 278°–280° C.

If the same method is carried out without adding ammonium chloride, the yield of pure product is 35% of theory.

EXAMPLE 24(e)

18.3 g (0.1 mol) of 1-benzyl-2-cyanoimidazole are dissolved in 80 ml of ethanol, mixed with 5.0 g (0.1 mol) of hydrazine monohydrate in 30 ml of ethanol, and refluxed for 20 hours. The mixture is then left to cool to room temperature and the amidrazone formed is treated with nitrous acid by first adding, dropwise, a solution of 6.9 g (0.1 mol) of sodium nitrite in 30 ml of water and then 100 ml of 1 N hydrochloric acid (0.1 mol) over 2 hours, the reaction temperature being kept below 25° C. by cooling. The mixture is stirred for a further hour, filtered from the precipitated product, which is washed with water and then ethanol, and subsequently recrystallised from dimethylformamide.

Yield: 9.5 g (42% of theory); m.p. 278°–280° C.

EXAMPLE 25(b)

2-(5-Tetrazolyl)-imidazole

Prepared by hydrogenolytic debenzylation of 1-benzyl-2-(5-tetrazolyl)-imidazole (the product of Example 24) using the process according to Example 13(b). Yield 51% of theory, m.p. 320°–321° C. (decomp.).

EXAMPLE 49

1-Methyl-2-(2-methyl-5-tetrazolylmethyl)-imidazole-hydrochloride (formula VI (cf. formula sheet)) and

EXAMPLE 50

11-Methyl-2-(1-methyl-5-tetrazolylmethyl)-imidazole (formula VII (cf. formula sheet)

8.2 g (50 mmol) of 1-methyl-2-(5-tetrazolylmethyl)-imidazole from Example 1 are dissolved in 200 ml of methanol and 10 ml of water, and freshly prepared ethereal diazomethane solution is added until there is a lasting yellow coloration and nitrogen evolution has ceased. After removal of the solvent under reduced pressure, 8.9 g (100% of theory) of oily crude product are obtained which crystallises out on being left to stand. According to analysis by thin-layer chromatography on silica gel 60 $F_{254}$ with chloroform/methanol (volume ratio=9:1) as the eluant, it is a binary mixture of isomers which can be separated by chromatography on a silica gel 60 column (diameter 5 cm, height 120 cc) using the same eluant. The structures of the isomers are readily discovered by means of proton-n.m.r. spectroscopy (cf. inter alia: E. Balieu and N. A. Klitgaard, Acta. Chem. Scand. 26, 2951 (1972)). According to the n.m.r. spectra, the isomer methylated in the 2-position of the tetrazole ring passes through the column first.

Yield: 2.9 g (32.6% of theory) of oily product which cannot be obtained in crystalline form until after conversion into the hydrochloride; m.p. 140° C. (from isopropanol);

Analysis: calculated for $C_7H_{11}ClN_6$: C 39.17; H 5.17 Cl 16.51; N 39.15. found: C 39.04; H 5.20; Cl 16.48; N 39.12.

The isomer with the tetrazole nucleus methylated in the 1-position is obtained as a residue after evaporation of the solvent and can be recrystallised from ethyl acetate.

Yield: 3.4 g (38.2% of theory); m.p. 147°–148° C.;

Analysis: calculated for $C_7H_{10}N_6$: C 47.18; H 5.66; N 47.16. found: C 47.25; H 5.65; N 47.04.

EXAMPLE 51

1-Benzyl-2-(2-methyl-5-tetrazolyl)-imidazole (m.p. 73°–74° C.) and

EXAMPLE 52

1-Benzyl-2-(1-methyl-5-tetrazolyl)-imidazole (m.p. 110°–111° C.) are obtained as described above by methylation of 1-benzyl-2-(5-tetrazolyl)-imidazole obtained in Example 24, suspended in aqueous methanol, with diazomethane, and subsequent separation by column chromatography of the binary mixture of isomers formed on silica gel 60 with chloroform as eluant.

It is to be noted for the purpose of this divisional application the term "aryl" as used herein is limited to carbocyclic aryl. Moreover for the purpose of this divisional application the 6-membered heteroaromatic ring being or contained in $R^1$ is unsubstituted and no further substituent is present.

It is not intended that the examples given herein should be construed to limit the invention thereto, but rather they are submitted to illustrate some of the specific embodiments of the invention. Resort may be had to various modifications and variations of the present invention without departing from the spirit of the discovery or the scope of the appended claims.

formula sheet

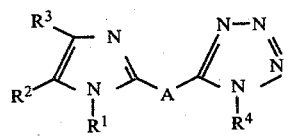 (I)

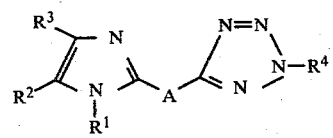 (II)

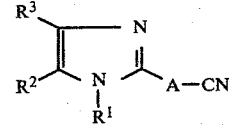 (III)

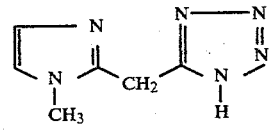 (IV)

-continued (V), (VI), (VII), (VIII) [chemical structures]

What we claim is:

1. A physiologically-acceptable compound of one of the formulae (I), (II) [chemical structures]

wherein

R¹ is a member selected from the group consisting of (a) a 6-membered heteroaromatic ring with up to two ring hetero atoms, each of which is a nitrogen atom, and (b) an alkyl group containing from 1 to 4 carbon atoms and substituted by such a heteroaromatic ring;

each of $R^2$ and $R^3$ is, independently, a hydrogen atom, alkyl having up to 4 carbon atoms, substituted or unsubstituted aryl or, together with the other of $R^2$ and $R^3$, unsubstituted —CH=CH—CH=CH— or —CH=CH—CH=CH— substituted by a member selected from the group consisting of alkyl having up to 4 carbon atoms, alkoxy having up to 4 carbon atoms, haloalkyl having up to 4 carbon atoms, halo and nitro;

$R^4$ is a member selected from the group consisting of a hydrogen atom, alkyl having up to 4 carbon atoms, aryl and aralkyl having up to 4 carbon atoms in the alkyl moiety; and A is a single bond or alkylene having from 1 to 6 carbon atoms;

any substitutent of substituted aryl being a member selected from the group consisting of alkyl having up to 4 carbon atoms, alkoxy having up to 4 carbon atoms, haloalkyl having up to 4 carbon atoms, halo or nitro;

or a physiologically-acceptable salt thereof.

2. A compound according to claim 1 which is a member selected from the group consisting of 1-(2-pyridyl)-2-(5-tetrazolyl)-imidazole and 1-(2-picolyl)-2-(5-tetrazolyl)-imidazole.

3. A physiologically-acceptable compound or salt of formula I according to claim 1.

4. A physiologically-acceptable compound or salt according to claim 1 wherein A is alkylene.

5. A physiologically-acceptable compound or salt according to claim 1 wherein A is a single bond.

6. A pharmaceutical composition having an active component in association with a pharmaceutical carrier or excipient and wherein the active component comprises from 10 to 1000 milligrams of a compound according to claim 1 or of a salt thereof.

7. A pharmaceutical composition according to claim 6 in unit-dosage form and wherein each dosage unit comprises from 10 to 200 milligrams of the compound or of a salt thereof.

8. A phamaceutical composition for treating a purine metabolic disorder and having an active component in association with a pharmaceutical carrier or excipient, the active component comprising an antiuricopathic effective amount of a pharmacologically-acceptable compound according to claim 1 or of a physiologically-acceptable salt thereof.

* * * * *